United States Patent [19]

Farmer et al.

[11] Patent Number: 5,136,088
[45] Date of Patent: Aug. 4, 1992

[54] SULFONATION PROCESS FOR VISCOUS SULFONIC ACID

[75] Inventors: David E. Farmer; Norman C. Foster, both of Seattle, Wash.; Thomas J. Loughney, Midland, Mich.; William B. Sheats; Ronald K. Borrevik, both of Seattle, Wash.

[73] Assignee: The Chemithon Corporation, Seattle, Wash.

[21] Appl. No.: 571,751

[22] Filed: Aug. 23, 1990

[51] Int. Cl.$^5$ .......................................... C07B 309/00
[52] U.S. Cl. ........................................ 562/88; 562/30
[58] Field of Search ..................................... 562/88, 30

[56] References Cited

U.S. PATENT DOCUMENTS 2,923,728  2/1960  Falk et al. .
3,620,684  11/1971 Brooks et al. .
4,113,438  9/1978  Brooks et al. ........................ 562/88

Primary Examiner—Jose G. Dees
Assistant Examiner—Keith D. MacMillan
Attorney, Agent, or Firm—Marshall, O'Toole, Gerstein, Murray & Bicknell

[57] ABSTRACT

A process is provided for sulfonating an organic reactant which, upon sulfonation, produces a viscous sulfonation reaction product having a viscosity substantially greater than 1,500 centipoises at a reaction temperature wherein the sulfonation reaction product is more than 85% by weight completely reacted. The process utilizes an elongated, enclosed reactor surface greater than about 15 feet in length having upstream and downstream ends and equipped with a heat exchanging surface. The process comprises cocurrently flowing a film of organic reactant and a gaseous sulfonating agent downwardly in the reactor while pressurizing the sulfonating agent cocurrently along said reactor surface while providing a pressure drop between upstream and downstream ends of the reactor to impart sufficient velocity to the gaseous sulfonating agent to thin the film of the viscous sulfonation product. The reactor surface is provided with sufficient length to subject the film to contact with the high velocity gaseous mixture for sufficient time to produce a sulfonation reaction product which is greater than about 85% by weight completely reacted.

18 Claims, No Drawings

SULFONATION PROCESS FOR VISCOUS SULFONIC ACID

BACKGROUND

The present invention relates to a process and apparatus for the sulfonation of organic reactants and particularly to an improved process and apparatus for the production of sulfonic acids such as alkyl diaryl ether disulfonic acid, alkyl diaryl disulfonic acid, high molecular weight alkyl aryl sulfonic acids, dialkyl aryl sulfonic acid and other sulfonic acids characterized by high viscosities at reaction conditions as compared to dodecylbenzene sulfonic acid.

The terms "sulfonation" and "sulfonating" as employed herein are used sometimes in their generic sense as applying both to true sulfonating and to sulfating, and sometimes in its specific sense, that is to true sulfonating. Where the context in which the terms "sulfonation" and "sulfonating" are used does not require the specific sense, it is to be construed generically.

Organic sulfonic acids and organic sulfonates are important commercially as components of detergents. Of interest to the present application is the disclosure of co-owned U.S. Pat. No. 3,620,684 to Brooks, et al. This patent discloses an improved method and apparatus for the sulfonation of organic reactants by means of a reaction between a liquid organic reagent and sulfur trioxide vapor in a thin-film reactor. The apparatus for carrying out the reaction comprises two externally cooled, concentric circular reaction surfaces, the space between the reaction surfaces being one-eighth to one-half inch; a rotor located concentrically between the two reaction surfaces, the clearance between the rotor and the reaction surfaces being five- to forty-thousandths (0.005 to 0.040) of an inch; means for turning the rotor; and means for passing the reactant liquid and the reactant gas in parallel streams to the space between the said reaction surfaces and the rotor. Also of interest is the disclosure of Falk, et al., U.S. Pat. No. 2,923,728 relating to a process of reacting organic compounds with sulfur trioxide.

Other methods for the sulfonation of organic products include the use of what are known in the art as "jet-reactors." See Brooks, et al., U.S. Pat. No. 4,113,438. The use of both thin-film and jet reactors for the sulfonation of organic reagents is generally suitable for reaction of reactants whose sulfonic acids have relatively low viscosities (10 to 1000 cps with a maximum of 1,500 cps at the temperature of reaction). The use of such reactors is limited, however, in cases where the sulfonation reaction produces a sulfonic acid having a high viscosity at the reaction temperature. Sulfonation products such as alkyl diphenyl ether disulfonic acid (ADEDS) are characterized by viscosities ranging from 1,500 cps to 40,000 cps at reaction temperature (about 200° F). ADEDS is particularly useful as an additive in household detergent formulations as well as a surfactant in many industrial detergent applications. As a detergent, ADEDS is characterized by excellent properties including high thermal stability, high solubility and the ability to solubilize other detergents. When produced according to conventional methods, however, ADEDS is generally unsuitable for household use because of residual processing impurities. Another sulfonation product characterized by high viscosity is high molecular weight alkyl benzene sulfonic acid (ABS) with an alkyl group of 18 or more carbons. ABS is particularly useful as a non-aqueous detergent such as an additive for high temperature lubricating oil. Another sulfonation product characterized by high viscosity is dialkyl naphthalene sulfonic acid (DANS) with each alkyl group containing 5 or more carbons. In its neutral form, DANS is particularly useful as a corrosion inhibiting agent.

All of the above described sulfonic acids are currently produced with batch solvent reaction systems. Most solvents used in such systems are hazardous materials which must be contained, recovered and in some cases must be removed from the product because even small amounts remaining in the product are undesirable. Unfortunately, complete removal of such solvents from the product is extremely difficult if not impossible.

In the case of currently used film reactors, the thick films of high viscosity reaction products prevent sufficient penetration of the sulfur trioxide through the thickness of the reaction product to the unreacted feedstock to give sufficient yields of reaction products. Efforts to increase yields of the sulfonation reaction by means of applying higher temperatures or higher mole ratios of sulfur trioxide have generally proven to be of limited use. Addition of acetic acid is known to increase the reaction yields as is known with other alkyl aryl feedstocks.

SUMMARY OF THE INVENTION

The present invention provides an improved process for sulfonating an organic reactant which, upon sulfonation with a gaseous sulfonating agent (preferably sulfur trioxide), produces a viscous sulfonation reaction product having a viscosity substantially greater than 1,500 centipoises at reaction conditions. The method is capable of producing such a sulfonation reaction product which is greater than 85% by weight completely reacted. In particular, for dodecyl diphenyl ether (DDE), the method is capable of producing sulfonation reaction product which is greater than 88% by weight disulfonated.

The method of the invention comprises the steps including: providing an elongated, enclosed reactor surface greater than about 15 feet in length having upstream and downstream ends and equipped with a heat exchanging surface; flowing a film of the organic reactant along the reactor surface from the upstream end to the downstream end; directing a gaseous sulfonating agent cocurrently alongside the film; confining the gaseous sulfonating agent in close proximate relation to the film. A film of organic reactant is reacted with the gaseous sulfonating agent to form a film of sulfonated reaction product such that the film increases in viscosity progressively in a downstream direction as the extent of reaction and quantity of sulfonated reaction product increase.

The method of the invention calls for providing a pressure drop between the upstream and downstream ends of the reactor which is sufficient to impart to the gaseous agent an increasing velocity progressively in a downstream direction. The pressure drop results in an increasing velocity in a downstream direction because a given weight of gas under lower pressure at a downstream portion of the reactor has a greater volume than that gas at a higher pressure upstream portion of the reactor. This greater volume of gas must accordingly move with a greater velocity in order to progress through the reactor. The increasing velocity of the gaseous agent is utilized to thin the increasingly viscous film of reaction product so as to increase the reaction product surface area and reduce the degree of penetration through the reactant/product film required for the sulfonating agent to react to form product. The process of the present invention provides sulfonation product with yields in excess of 85% by weight by means of increased sulfonating agent/air mixture pressures, increased pressure drops and gas velocities through the reactor, and reactors having increased lengths but characterized by relatively small equivalent diameters. The reaction conditions are preferably selected to produce a sulfonation reaction product which is greater than about 88% by weight completely reacted, and most preferably greater than about 90% by weight completely reacted. Most preferably, the reaction conditions are selected to produce sulfonation reaction products which are approximately 100% monosulfonated and greater than 88% disulfonated on a mole basis.

DETAILED DESCRIPTION

The present invention provides an improved process for the sulfonation of organic reagents and particularly those where the sulfonation products are characterized by high viscosities. The process provides high sulfonation yields in sulfonation reactions where the sulfonation product is characterized by viscosities in excess of 1,500 centipoises at reaction conditions. A product of the present invention is ADEDS which, when produced according to the methods of the invention, is suitable for use in household detergents and industrial products.

The process of the present invention resolves the problem of reduced reactivity caused by the high viscosity of certain sulfonation products. The effect of the reduced reactivity is evident in the low yields or incompletely reacted product from conventional film and jet reactors. Although sulfur trioxide reacts rapidly with most sulfonatable organic feedstocks, the reaction rate can be severely limited by the decreased ability of sulfonating agents such as sulfur trioxide to penetrate through viscous product to unreacted sites. As the liquid reactant moves along the film reactor surface, the material becomes increasingly viscous as the sulfonation reaction proceeds. This causes the viscous product to increase in thickness on the reactor surface, inhibiting the sulfonation reaction and the passage of the gaseous agent through the reactor. By providing the gaseous agent at an adequate differential pressure to ensure passage of the gaseous agent through the reactor, the reaction product layer is thinned by the sheering action of the expanding gaseous agent as it proceeds from the high to low pressure ends of the reactor. The thinned layer of the reaction product reduces the degree of penetration required for the sulfonating agent to contact unreacted sites. Accordingly, with proper reactor sizing and selection of reaction conditions, commercial acceptable products can be produced at high reaction yields.

The process of the present invention provides sulfonation product with yields in excess of 85% by weight by means of increased sulfonating agent/air mixture pressures, increased pressure drops and gas velocities through the reactor and reactors having increased lengths but characterized by relatively small equivalent diameters, reduced liquid loading (mass flow per unit of reactor circumference) and higher film temperatures as manifested by higher reactor wall temperatures. While not wishing to be bound by any theory of the invention, it is believed that this combination of elevated pressure, pressure drop and gas velocities improve mixing and increase the kinetics of the sulfonation reaction thus improving the sulfonation yield.

Suitable Reactors

Reactors suitable for use according to the present invention include virtually all falling film reactors wherein cocurrent flow of liquid and vaporphase reactants may be maintained including multitube, parallel plate and annular reactors. While the method of the invention is preferably carried out in falling film reactors having vertically disposed reactor surfaces, the high velocity of the flowing gas renders it possible to dispose the reactor surfaces in orientations other than strictly vertical. In order to provide a sufficient residence time for the reactants, the lengths of reactors used according to the present invention must preferably be longer, in the range of from two to five-times, than those wherein reactions are carried out under lower pressure-drop or lower vapor flowrate conditions. Accordingly, the length of the surface where reaction occurs within the reactors is preferably between about 15 and about 60 feet and most preferably between about 20 and about 40 feet. Whatever length of reactor is chosen, it is important to maintain a relatively small equivalent diameter for the reactor in order that an adequate velocity of the gaseous agent can be generated such that a buildup of thickness of reaction product on the reactor surface does not occur. (Equivalent diameter=4 times the hydraulic radius=4 times the (cross-sectional area divided by the wetted perimeter length). Generally, the equivalent diameter should be maintained as less than about 0.8 inches, and greater than about 0.2 inches with about 0.5 inches particularly preferred.

Reaction Temperature

The method of the invention is sensitive with respect to reaction temperature such that the optimum temperature for reaction may be neither too hot nor too cold. In reactions for the production of ADEDS, the optimum input temperature for the liquid organic reactant ranges from about 60° to about 200° F. and preferably from about 90° to about 130° F., with the preferred input temperature of the gaseous sulfonating agent ranging from about 90° to about 200° F. and most preferably from about 100° to about 120° F. Because heat is generated in the course of the exothermic sulfonation reaction, a heat exchanging surface is generally required to control the temperature of the reactor. A preferred temperature range for heat transfer fluid in the cooling jacket contacting the reactor walls ranges from about 180° F. to about 220° F. Hotter heat transfer fluid tends to reduce the viscosity of the reaction product in the thin film but can induce the production of undesired oxidation by-products. On the other hand, cooler heat transfer fluid removes more heat from the reactor and reduces the rate of side reactions but increases the viscosity of the film of reaction product which inhibits penetration of sulfur trioxide and leads to a less-completely reacted product. Although the optimum reaction temperature will naturally vary for any given combination of reactants and reactor, it is well within the ordinary level of skill in the art to determine the optimum temperature range for a given set of reaction conditions.

Reaction Pressure

The method of the invention requires a high inlet pressure in the range of about 30 psig to 150 psig because of the requirement that there be a large pressure drop between the upstream and downstream ends of the reactor surface. It is this pressure drop which imparts a relatively high velocity to the gaseous sulfonating agent and enables it to strip away a substantial portion of the thickness of the layer of viscous reaction product. It is preferred that dry tube gas velocities be maintained in excess of about 40 feet per second at the upstream end of said reactor surface (reactor inlet) and in excess of about 200 feet per second at the downstream end of said reactor surface (reactor outlet). In the course of the sulfonation reaction, the thickness of the film or reaction product on the walls of the reactor gradually increases as the feedstock and product materials flow to the bottom of the reactor. As the thickness of the reaction product increases, the area of the reactor available for gas flow gradually decreases, thus restricting the gas flow and increasing the gas velocity. In addition, the drop in pressure leads to expansion of the gas, further increasing the velocity of gas flow. While the velocity of the gas may approach the speed of sound, it will not exceed that velocity. Accordingly, preferred pressure drops range from about 90 psi to about 120 psi where the feedstock is a branched precursor of ADEDS, but may be in the range of from about 70 psi to about 100 psi where the feedstock is a linear precursor of ADEDS.

Reactor outlet gas pressure is generally less than about 15 psig but depends on the degree of pressure drop required by downstream effluent gas processing equipment. Outlet pressures preferably range from about 5 to about 15 psig where the reactor discharge is to a gas-liquid separator but can be as low as 0 psig where the discharge is not directly to another piece of processing equipment.

In addition to increasing the pressure and pressure drop within the reactor, the total mass of gas added to the reactor is increased over that used by prior art methods by adding more diluent air to the reaction vapor. The method of the present invention preferably utilizes feed gas with a sulfonating agent (preferably sulfur trioxide) concentration ranging from about 1.4% to about 10.0% by volume, with concentrations ranging between about 1.4% and about 4.0% being preferred and concentrations of about 2.5% sulfur trioxide being particularly preferred.

The reaction product is discharged from the reactor at a temperature of about 200° F. Unlike certain prior art processes, it is preferred that cooled reaction product not be recycled to the reactor. While recycling material will not necessarily hurt the reaction, the reaction product tends to be so viscous that it cannot readily be pumped to the reactor for recycling.

While the method of the present invention is particularly preferred for the production of ADEDS, it is generally useful for use with feedstocks which produce other viscous reaction products having viscosities greater than 1,500 centipoises at reaction temperatures which, because of their viscosity, cannot be readily sulfonated without the use of solvents such as $C_6$ to $C_{20}$ hydrocarbons or various halogenated hydrocarbons. The method of the invention is thus useful in the production of monosulfonates by sulfonation of feedstocks comprising dialkyl benzenes having $C_8$–$C_{20}$ sidechains, dialkyl toluenes having $C_8$–$C_{20}$ sidechains, alkyl benzenes having $C_{18}$–$C_{40}$ sidechains, polyisopropyl naphthalenes with molecular weights ranging from 300 to 600, isobutanes with total molecular weights ranging from 300 to 500, dialkyl phenols with $C_6$–$C_{12}$ sidechains, dialkyl naphthalenes with $C_6$–$C_{12}$ sidechains (which can also be disulfonated), $C_6$–$C_{18}$ cocomonoglycerides (ester of coconut fatty acids and glycerine). Feedstocks which can be disulfonated include biphenyl alkanes with $C_6$–$C_{18}$ alkane groups, diphenyl ether, diphenyl alkanes with $C_6$–$C_{18}$ alkane groups, alkyl benzene sulfones with $C_6$–$C_{18}$ sidechains. It would be necessary to vary specific process parameters according to the identity of the sulfonation feedstock utilized. In light of the basic teachings of the present invention, however, such adjustment would be well within the ordinary skill in the art. Products produced by sulfonation of the above feedstocks are useful as lubricating oil additives, corrosion inhibitors and wetting agents.

In the following examples, a film reactor was used to carry out a sulfonation reaction on alkyl diphenyl ether feedstocks according to the method of the invention. The film reactor had a 25 foot vertical reactor surface and was operated without a recycle quench to react a feedstock with a sulfur trioxide gas mixture. In the examples, the cooling water temperature is indicated for water on a single reactor cooling surface, although in certain indicated situations, multiple segment reactor cooling surfaces having different temperatures were found to be useful.

EXAMPLE 1

In this example, branched dodecyl diphenyl ether BDDE feedstock was reacted with sulfur trioxide in the 25 foot vertical film reactor according to the method of the invention as well as in a standard 5 foot film reactor under the conditions specified in Table 1. While the method of the invention yielded a product that was 90% and greater (mole basis) disulfonated, the standard 5 foot reactor yielded a product with a degree of disulfonation (63%) unsuitable for commercial use.

EXAMPLES 2 AND 3

In these examples, linear dodecyl diphenyl ether (LDDE) and branched octadecyl benzene (BODAB) feedstocks were reacted with sulfur trioxide in the 25 foot film reactor according to the method of the invention. The results of those reactions are shown in Table 1 below.

TABLE 1

| Example | Feedstock* | SO₃ Inlet Conc. (Vol. %) | Mole Ratio (SO₃/Feed) | Feed (lb/hr) | Reactor Length (ft) | Reactor Diameter (inch) | Temperatures (°F.) Inlet SO₃ | Temperatures (°F.) Inlet Feed | Temperatures (°F.) Cooling Water | Pressure Drop (psi) | Disulfonate (mole %) | Monosulfonate (mole %) | $H_2SO_4$ (wt. %) | Disulfonate (wt. %) | Monosulfonate (wt. %) |
|---|---|---|---|---|---|---|---|---|---|---|---|---|---|---|---|
| 1A | BDDE | 2.5 | 2.2 | 16.4 | 25 | 0.5 | 100 | 100 | 200 | 114 | 90 | 10 | 2 | 89 | 9 |
| 1B | BDDE | 2.5 | 2.3 | 15.8 | 5 | 0.6 | 190 | 190 | 170 | 48 | 63 | 37 | 2 | 65 | 32 |
| 2A | LDDE | 2.5 | 2.1 | 17.8 | 25 | 0.5 | 110 | 110 | 175 | 80 | 93 | 7 | 2 | 90 | 5 |

TABLE 1-continued

| | | SO₃ Inlet Conc. (Vol. %) | Mole Ratio (SO₃/ Feed) | Feed (lb/ hr) | Reactor Length (ft) | Reactor Diameter (inch) | Temperatures (°F.) | | | Pressure Drop (psi) | Analysis | | | | |
|---|---|---|---|---|---|---|---|---|---|---|---|---|---|---|---|
| | | | | | | | Inlet | | Cooling Water | | Disulfonate (mole %) | Monosulfonate mole % | $H_2SO_4$ (wt. %) | Disulfonate (wt. %) | Monosulfonate (wt. %) |
| Example | Feedstock* | | | | | | SO₃ | Feed | | | | | | | |
| 3A | BODAB | 2.7 | 1.0 | 43.9 | 25 | 0.6 | 110 | 140 | 140 | 60 | — | — | 1 | — | 85 |

*BDDE (branched dodecyl diphenyl ether)
LDDE (linear dodecyl diphenyl ether)
BODAB (branched octadecyl benzene)

The methods of the present invention may be practiced with a wide variety of feedstocks under varying conditions chosen according to the specific nature of those feedstocks. From the foregoing description, one of skill in the art will recognize numerous changes and modifications of the invention to adapt it to particular materials and conditions. Consequently, only such limitations should be placed on the invention as appear in the following claims.

What is claimed is:

1. In a process for sulfonating an organic reactant which, upon sulfonation, produces a viscous sulfonation reaction product having a viscosity substantially greater than 1,500 centipoises at reaction conditions, a method for producing such a sulfonation reaction product which is greater than about 85% by weight completely reacted, said method comprising the steps of:
   providing an elongated, enclosed reactor surface greater than about 15 feet in length having upstream and downstream ends and equipped with a heat exchanging surface;
   flowing a film of said organic reactant along said reactor surface from said upstream end to said downstream end;
   directing a gaseous sulfonating agent cocurrently in contact with said film for greater than about 15 feet;
   confining said gaseous sulfonating agent in close, proximate relation to said film;
   pressurizing siad gaseous sulfonating agent to a pressure level greater than about 30 psig and providing a pressure drop, between said upstream and downstream ends of said reactor surface, sufficient to impart to said gaseous sulfonating agent a relatively high velocity which strips away at least a substantial portion of the thickness of said film to breakup said film; and
   reacting said film and said high velocity gaseous mixture for a period of time sufficient to produce a sulfonation reaction product, at said downstream end which is greater than about 85% by weight completely reacted;
   wherein said organic reactant is selected from the group consisting of dialkyl benzenes having $C_8$-$C_{20}$ sidechains, alkyl toluenes having $C_8$-$C_{20}$ sidechains, alkyl benzenes having $C_{18}$-$C_{40}$ sidechains, polyisopropyl naphthalenes with molecular weights ranging from 300 to 600, isobutanes with molecular weights of 300 to 500, dialkyl phenols with $C_6$-$C_{12}$ alkyl groups, dialkyl naphthalenes with $C_6$-$C_{12}$ sidechains, $C_6$-$C_{12}$ cocomonoglycerides, biphenyl alkanes with $C_6$-$C_{18}$ alkane groups, alkyl diphenyl ethers with a $C_6$ to $C_{18}$ alkyl group, biphenyl alkanes with a $C_6$ to $C_{18}$ alkane group, and alkyl benzene sulfones with $C_6$ to $C_{18}$ sidechains.

2. The process of claim 1 wherein the inlet gas pressure in said reactor is from about 30 psig to about 150 psig and the outlet gas pressure in said reactor is less than about 15 psig.

3. The process of claim 1 wherein the dry tube gas velocity at the upstream end of said reactor surface is greater than about 40 feet per second.

4. The process of claim 1 wherein the dry tube gas velocity at the downstream end of said reactor surface is greater than 200 feet per second.

5. The process of claim 1 wherein the inlet temperature of the organic reactant is between about 60 and 200° F.

6. The process of claim 1 wherein the inlet temperature of the gaseous sulfonating agent is between about 90° F. and 200° F.

7. The process of claim 1 wherein the reactor surface is between about 15 and 60 feet in length.

8. The process of claim 1 wherein the reactor surface is vertically disposed.

9. The process of claim 1 wherein the reactor surface is between about 20 and 40 feet in length.

10. The process of claim 1 wherein the equivalent diameter of the reactor is between about 0.2 inches and about 0.8 inches.

11. The process of claim 10 wherein the equivalent diameter of the reactor is about 0.5 inches.

12. The process of claim 1 wherein the gaseous sulfonating agent comprises sulfur trioxide.

13. The process of claim 1 wherein said sulfur trioxide has a concentration between 1.4% and 10.0% by volume.

14. The process of claim 1 wherein said sulfur trioxide has a concentration between 2.0% and 7.0% by volume.

15. The process of claim 1 wherein said organic reactant is a alkyl diphenyl ether with a $C_6$ to $C_{18}$ alkyl group.

16. The process of claim 1 wherein the sulfonation reaction product is greater than about 99% mono- or disulfonated and greater than 88% disulfonated on a mole basis.

17. The process of claim 1 wherein said organic reactant is selected from the group consisting of dialkyl benzenes having $C_8$-$C_{20}$ sidechains, alkyl toluenes having $C_8$-$C_{20}$ sidechains, alkyl benzenes having $C_{18}$-$C_{40}$ sidechains, polyisopropyl naphthalenes with molecular weights ranging from 300 to 600, isobutanes with molecular weights of 300 to 500, dialkyl phenols with $C_6$-$C_{12}$ alkyl groups, dialkyl naphthalenes with $C_6$-$C_{12}$ sidechains, $C_6$-$C_{12}$ cocomonoglycerides and biphenyl alkanes with $C_6$-$C_{18}$ alkane groups.

18. The process of claim 1 wherein said organic reactant is a biphenyl alkane with a $C_6$ to $C_{18}$ alkane group.

* * * * *